United States Patent [19]

Pesa et al.

[11] 4,271,038
[45] Jun. 2, 1981

[54] CATALYSTS FOR THE HYDROFORMYLATION OF OLEFINICALLY UNSATURATED COMPOUNDS

[75] Inventors: Frederick A. Pesa, Aurora; Thomas A. Haase, University Heights, both of Ohio

[73] Assignee: Standard Oil Company, Cleveland, Ohio

[21] Appl. No.: 104,644

[22] Filed: Dec. 17, 1979

[51] Int. Cl.³ .............................................. B01J 31/22
[52] U.S. Cl. ................................ 252/428; 252/431 C; 252/431 N; 260/465.9; 568/455
[58] Field of Search ................ 252/428, 431 N, 431 C

[56] References Cited

U.S. PATENT DOCUMENTS

| 2,951,799 | 9/1960 | Sharp | 252/431 N X |
| 2,966,453 | 12/1960 | Gleim et al. | 252/431 N X |
| 3,116,328 | 12/1963 | Cox et al. | 252/431 N X |
| 3,658,721 | 4/1972 | Tamaru et al. | 252/431 N X |

*Primary Examiner*—Patrick Garvin
*Attorney, Agent, or Firm*—Herbert D. Knudsen; Joseph G. Curatolo; Larry W. Evans

[57] ABSTRACT

This invention relates to the production of aldehydes by the addition of carbon monoxide and hydrogen to olefinically unsaturated compounds in the presence of a complex catalyst comprising cobalt carbonyl and a porphyrin promoter ligand. This process can be carried out under relatively mild conditions of temperature and pressure.

9 Claims, No Drawings

CATALYSTS FOR THE HYDROFORMYLATION OF OLEFINICALLY UNSATURATED COMPOUNDS

BACKGROUND OF THE INVENTION

The hydroformylation reaction involves the addition of a hydrogen atom and a formyl group to the double bond of an olefinic compound. In early applications of this reaction, a finely divided active cobalt metal prepared in much the same manner that a cobalt hydrogenation catalyst is made was used as the hydroformylation catalyst. It was soon discovered that cobalt carbonyl, which is formed quite readily by the action of carbon monoxide on an active metallic cobalt catalyst, is the active ingredient in the hydroformylation reaction. These cobalt carbonyl catalysts have been used extensively in the prior art either alone or in combination with various promoter ligands in order to produce aldehydes from olefins.

The major drawback to the use of the prior art catalyst systems, however, has been that these catalyst systems require high temperatures and high pressures for the reaction to proceed. Moreover, when an unsymmetrical olefin is used as the reactant at least two isomeric products, i.e. branched chain and straight chain, are obtained. No general method has been developed in the prior art for the control of the isomeric product composition.

The present invention overcomes these problems present in the prior art. In this regard, the inventive process results in higher conversions, higher yields and faster reaction rates than those disclosed in the prior art. Moreover, the instant invention is particularly selective for the straight chain isomeric product. Finally, the instant reaction proceeds under relatively mild conditions of temperature and pressure. These advantages can result in substantial cost savings in the production of aldehydes.

SUMMARY OF THE INVENTION

The instant invention provides a novel catalyst comprising a complex of cobalt carbonyl and a porphyrin promoter ligand. It has been discovered that aldehydes can be produced by contacting an olefinically unsaturated compound with carbon monoxide and hydrogen in the presence of this catalyst.

In particular, this invention relates to a hydroformylation process for the production of 3-cyanopropionaldehyde comprising contacting acrylonitrile, carbon monoxide and hydrogen gas in the presence of a complex catalyst comprising cobalt carbonyl and a porphyrin promoter ligand.

DETAILED DESCRIPTION

Hydroformylation reactions may be illustrated by the general equation:

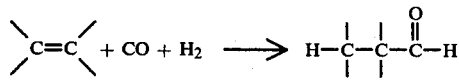

If the olefinic unsaturated hydrocarbon reactant is unsymmetrical, then this reaction results in both branched chain and straight chain products as illustrated by the following equation;

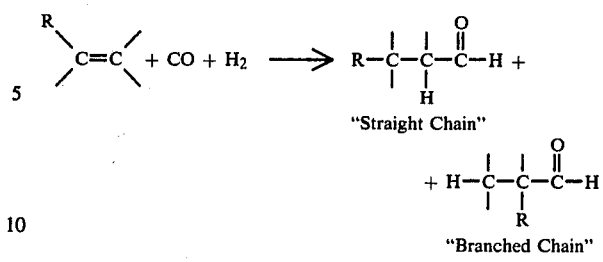

"Straight Chain"

"Branched Chain"

The catalyst of this invention is particularly selective for the straight chain isomer product.

Reactants

The inventive reaction proceeds by contacting an olefinically unsaturated compound, carbon monoxide and hydrogen. These reactants must all be present in some form for the reaction to proceed.

The hydroformylation reaction has been applied to a wide variety of olefinically unsaturated compounds including hydrocarbons, alcohols, esters, ethers, acetals, nitriles and the like. This invention is, of course, applicable to any of the olefinic compounds that can be employed in a hydroformylation reaction. In general, olefinic compounds with functional groups can be hydroformylated provided the functional groups do not react with the catalyst in such a manner as to nullify the action of the catalyst. Moreover, a functional group which reacts with the aldehyde will lead to secondary products after the initial hydroformylation reaction.

Preferred olefinically unsaturated compounds are those wherein ethene, i.e. $H_2C=CH_2$, is substituted with one or more of the compounds selected from the group consisting of $C_{1-10}$ alkyls; $—(CH_2)_p—CN$, wherein p is 0–3; and $—(CH_2)_q—OH$, wherein q is 1–10. Most preferably, the ethene is substituted with one of methyl or $—(CH_2)_p—CN$, wherein p is 0 or 1.

Representative olefinically unsaturated hydrocarbons suitable for use herein include ethene, propene, 1-hexene, cyclohexene, acrylonitrile, 2-heptene, 3-ethylpentene-1, 2-methylpentene-2, cyclopentene, di-isobutylene and 1-dodecene. This reaction proceeds particularly well when acrylonitrile is the olefinically unsaturated hydrocarbon.

Substantial partial pressures of carbon monoxide and hydrogen are required for the reaction to proceed. The use of the instant promoter ligand permits satisfactory operation at system pressures in the range of from about 100 to 2,500 psi with the corresponding temperature being about 50° C. to 150° C. Suitable relative proportions of hydrogen to carbon monoxide being in the range of 0.5–10 to 1 respectively, and preferably 1–3 to 1. Preferably, the carbon monoxide and hydrogen gas is added to the reaction system in the form of a synthesis gas (an equal molar mixture of CO and $H_2$).

Process Conditions

The inventive reaction can be accomplished in either the batch mode or continuously. The reaction temperature is normally maintained between 50° C. and 150° C., preferably between 70° C. and 110° C. The reaction pressure is normally maintained at 100 to 2,500 psi, preferably at 700 to 1,300 psi. When the reaction is carried out in the batch mode, the reactants and catalysts are contacted with one another for a period of 10 minutes to 6 hours, preferably ½ hour to 4 hours. The reaction time of less than 10 minutes or more than 6 hours can be used if desired, although better results will be obtained if the reaction time is maintained within this range. When the process is carried out on a continuous basis, the reaction contact time is normally 10 seconds to 10 minutes, preferably 100 seconds to 5 minutes.

Normally, an inert solvent is used in carrying out the process of this invention. The inert solvents that are used as the reaction media are non-reactive with the hydroformylation catalyst and with the reactants and products of the hydroformylation reaction. Preferred solvents are free of olefinic and acetylenic unsaturated bonds and they contain only carbon, hydrogen and oxygen atoms. Among the solvents that can be used are aromatic hydrocarbons such as benzene, toluene, xylene, ethylbenzene, tetralin and the like. Also, ethers such as diethylether, dibutylether, anisol, diphenylether and dioxane can be used. Esters such as ethylacetate, methylbenzoate, diethyladipate and dioctyl phthalate can be used. Additionally, ether-esters such as methoxyethylacetate and butoxyethoxyethylacetate can be used.

Catalysts

The complex catalyst of the present invention is prepared by mixing cobalt carbonyl with a porphyrin promoter ligand. The molar ratio of the cobalt carbonyl to the porphyrin is about 0.1–20:1, preferably about 1–3:1. The ratio will vary depending upon the particular prophyrin chosen.

The porphyrin compounds which are preferably used in this invention can be represented by the following formula:

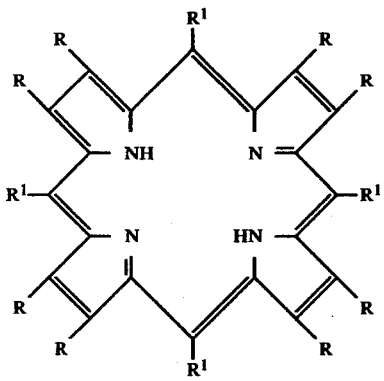

wherein each R can be independently selected from the group consisting of:
(1) H;
(2) $C_{1-8}$ alkyl;
(3) —$(CH_2)_y$—COOT, wherein y is 1–4 and T is H or a $C_{1-4}$ alkyl;
(4) $C_{1-8}$ alcohol radical;
(5) $C_{1-8}$ alkene radical;
wherein each $R^1$ can be independently selected from the group consisting of:
(1) H;
(2) phenyl;
(3) substituted phenyl substituted with one or more carboxy groups or $C_{1-4}$ alkyl groups or mixtures thereof.
Preferably R is selected from the group consisting of H, $CH_3$, $C_2H_5$, $CH=CH_2$, $CH_2$—COOH, $(CH_2)_2$—COOH, $CH(OH)CH_3$ and $(CH_2)_2$—COOCH$_3$;

and $R^1$ is selected from the group consisting of H, phenyl and carboxyphenyl.

Examples of suitable porphyrins include octaethylporphyrin, protoporphyrin, protoporphyrin dimethyl ester, meso-tetraphenylporphyrin, meso-tetra(4-carboxyphenyl)porphyrin, aetioporphyrin, deuteroporphyrin, haematoporphyrin, mesoporphyrin, coporphyrin and uroporphyrin.

The catalyst of this invention is dissolved in the reaction medium as a homogeneous catalyst. These homogeneous catalysts are prepared by known techniques. Specific preparation of these catalysts are shown in the working examples of the specification. Examples of the cobalt carbonyl component utilizable for the preparation of the complex catalyst of the present invention include cobalt carbonyl itself and cobalt compounds capable of forming cobalt carbonyl under the reaction conditions for hydroformylation. Examples of such cobalt compounds are cobalt carbonate, cobalt naphthanate and metallic cobalt.

The oxygenated organic compounds produced by this process are useful as plasticizers and as intermediates for alcohols and polymers.

SPECIFIC EMBODIMENTS

In order to more thoroughly illustrate the present invention, the following working examples are presented. In these examples the following definitions are used:

$$\% \text{ Conv.} = \frac{\text{Moles Carbon In Acrylonitrile Conv. To Prod.}}{\text{Moles Carbon In Acrylonitrile Fed}} \times 100$$

$$\% \text{ Yield} = \frac{\text{Moles Carbon of Acrylonitrile Conv. To Prod.}}{\text{Moles Carbon Of Acrylonitrile Fed}} \times 100$$

$$\text{Nat. Bal.} = \frac{\text{Moles Carbon In Reactants}}{\text{Moles Carbon In Prod. and Unreacted Reactant}} \times 100$$

EXAMPLES 1 THRU 6

13.5 gms. of acrylonitrile, 100 ml. of solvent and a preweighed portion of a porphyrin promoter ligand were placed into a glasslined autoclave. Next, 1.37 gms. of $Co(CO)_8$ was added and the autoclave sealed.

The autoclave was flushed 2 times with a 1 to 1 mixture of $CO/H_2$ and then charged with premixed synthesis gas to the desired pressure. The temperature was increased and the reaction was allowed to proceed for 1 to 5 hours. The autoclave was then brought to room temperature by cooling with cold water, depressurized and opened for product analysis. The process conditions, the acrylonitrile conversion and the product yields are shown in Table I.

Comparative Example A

The experimental procedure described in Examples 1 to 6 was followed except that tetramethyl-1,3-propanediamine was used as the promoter ligand instead of a porphyrin. The results are shown in Table I.

A comparison between the porphyrin promoted examples and Comparative Example A shows that the porphyrin examples have a much higher material balance. This higher material balance is due to the fact that porphyrins maintain high selectivities and yields while reducing the amount of polymerization of the products and reactants.

TABLE I

| | | Hydroformylation of Acrylonitrile | | | | | | |
|---|---|---|---|---|---|---|---|---|
| Example | Promoter Ligand | Cobalt Carbonyl/ Promoter Ligand (Molar Ratio) | Solv | Pres[1] (psi) | Temp (°C.) | Time (Hrs.) | % Conv of AN | % Yield 3-CPA | Material Balance (%) |
| 1 | TPP | 3:1 | DMP | 800 | 75 | 3 | 68.9 | 100.0 | 87.7 |
| 2 | OEP | 4:1 | DMP | 800 | 75 | 3 | 54.1 | 87.9 | 80.9 |
| 3 | CPP | 3:1 | MeBz | 800 | 75 | 5 | 43.5 | 100.0 | 81.5 |
| 4 | TPP | 3:1 | MeBz | 800 | 100 | 1 | 85.3 | 99.5 | 93.2 |
| 5 | TPP | 5:1 | MeBz | 800 | 75 | 2½ | 84.5 | 91.2 | 99.3 |
| 6 | TPP | 0.5:1 | DMP | 1200 | 95 | ½ | 100.0 | 86.5 | 79.4 |
| A | TMPD | 3:1 | DMP | 800 | 75 | 2 | 97.5 | 94.5 | 50.8 |

[1]CO/H$_2$ = 1/1

GLOSSARY

| | |
|---|---|
| 3-CPA | 3-cyanopropionaldehyde |
| CPP | meso-tetra(4-carboxyphenyl)porphyrin |
| DMP | dimethyl phthalate |
| MeBz | methylbenzene |
| OEP | octaethylporphyrin |
| TMPD | tetramethyl-1,3-propanediamine |
| TPP | meso-tetraphenylporphyrin |

Although only a few embodiments of the present invention have been specifically described above, it should be appreciated that many additions and modifications can be made without departing from the spirit and scope of the invention. These and all other modifications are intended to be included within the scope of the present invention, which is to be limited only by the following claims:

We claim:

1. A catalyst composition comprising cobalt carbonyl and a porphyrin promoter ligand, wherein the molar ratio of the cobalt carbonyl to the porphyrin promoter is in the range of about 0.1:1 to about 20:1.

2. The catalyst composition of claim 1 wherein the porphyrin promoter ligand is represented by the formula:

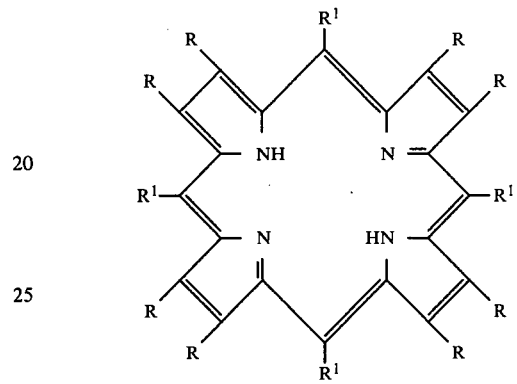

wherein each R can be independently selected from the group consisting of:
(1) H;
(2) C$_{1-8}$ alkyl;
(3) —(CH$_2$)$_y$—COOT, wherein y is 1-4 and T is H or a C$_{1-4}$ alkyl;
(4) C$_{1-8}$ alcohol radical;
(5) C$_{1-8}$ alkene radical;

wherein each R$^1$ can be independently selected from the group consisting of:
(1) H;
(2) phenyl;
(3) substituted phenyl substituted with one or more carboxy groups or C$_{1-4}$ alkyl groups or mixtures thereof.

3. The catalyst composition of claim 2 wherein R is selected from the group consisting of H, CH$_3$, C$_2$H$_5$, CH=CH$_2$, —CH$_2$—COOH, —(CH$_2$)$_2$—COOH, CH(OH)CH$_3$, (CH$_2$)$_2$COOCH$_3$ or mixtures thereof.

4. The catalyst composition of claim 2 wherein R$^1$ is selected from the group consisting of H, phenyl, carboxyphenyl or mixtures thereof.

5. The catalyst composition of claim 1 wherein the porphyrin is selected from the group consisting of octaethylporphyrin, meso-tetraphenylporphyrin and meso-tetra(4-carboxyphenyl)porphyrin.

6. The catalyst composition of claim 1 wherein the porphyrin is meso-tetra(4-carboxyphenyl)porphyrin.

7. The catalyst composition of claim 1 wherein the molar ratio of the cobalt carbonyl to the porphyrin promoter ligand is in the range of about 1:1 to about 3:1.

8. The catalyst composition of claim 5 wherein the molar ratio of the cobalt carbonyl to the porphyrin promoter ligand is in the range of about 0.5:1 to about 5:1.

9. The catalyst composition of claim 6 wherein the molar ratio of the cobalt carbonyl to the porphyrin promoter ligand is in the range of about 0.5:1 to about 5:1.

* * * * *